United States Patent [19]

Geho

[11] Patent Number: 4,602,043
[45] Date of Patent: Jul. 22, 1986

[54] TREATMENT FOR HYPOGLYCEMIA

[75] Inventor: W. Blair Geho, Wooster, Ohio

[73] Assignee: Technology Unlimited Inc., West Wooster, Ohio

[21] Appl. No.: 604,154

[22] Filed: Apr. 26, 1984

Related U.S. Application Data

[63] Continuation-in-part of Ser. No. 514,492, Jul. 18, 1983, abandoned.

[51] Int. Cl.$^4$ ............................................. A61K 31/135
[52] U.S. Cl. ..................................................... 514/646
[58] Field of Search ......................................... 514/646

[56]  References Cited
PUBLICATIONS

Merck Index, 9th Ed. 362–363 (1976).

Primary Examiner—Stanley J. Friedman
Attorney, Agent, or Firm—Frijouf, Rust & Pyle

[57]  ABSTRACT

This invention is for an improved method of treating the disease of hypoglycemia (low blood glucose), based on the discovery by the inventor of the etiology of the disease. The genesis of this invention is in the discovery that insulin alone does not control the uptake and regeneration of glucose by the liver. It has been discovered that hepatic storage of glucose following a meal requires the related function of insulin and serotonin. Hypoglycemia occurs during fasting and is due to an inappropriate release of serotonin to the liver. From this, the method of using a serotonin antagonist or an agent to block synthesis and/or storage of serotonin in timed relationship to ingested food to stop the action or the production of serotonin after glucose is no longer supplied to the portal vein is described. Then the liver can cease glucose uptake and begin production of glucose for the peripheral blood supply. The preferred antagonist is cyproheptadine.

3 Claims, 2 Drawing Figures

TREATMENT FOR HYPOGLYCEMIA

CROSS-REFERENCE TO RELATED APPLICATION

This application is a continuation-in-part of application Ser. No. 514,492 filed July 18, 1983, now abandoned.

BACKGROUND OF THE INVENTION

1. Field of the Invention

Therapeutic methods for control of low blood sugar levels in warm blooded animals, including humans.

2. Information Disclosure Statement

Glucose in the blood is a primary energy nutrient for the body. Its level in the blood is carefully controlled so that it neither goes too high nor too low. Maintaining a constant blood level of glucose is so important that the body has, within the limits of current understanding of physiology, surprisingly sophisticated hormonal systems to prevent both hyperglycemia (blood glucose too high) and hypoglycemia (blood glucose too low).

The body has diseases that are characterized by blood glucose levels that are either too high (i.e., Diabetes Mellitus types I and II) or too low (i.e., hypoglycemia). This disclosure describes improved therapeutic means to correct abnormally depressed blood glucose levels.

This invention recognizes the etiologies of these diseases of glucose metabolism. In order to understand the use of these new therapeutic inventions, it is necessary to describe the normal physiological control mechanisms of the body. Once they are understood, the etiologies of the disease states of hypoglycemia can be recognized. Finally, with all of this knowledge in place, the new therapies can be described.

Glucose is the main energy substance of the body and the blood is the means for transporting it to the various parts of the body. The blood glucose may be elevated by increasing its supply or blocking its removal. Conversely, blood glucose may be decreased by blocking its supply or enhancing its rate of removal from the blood.

There are two sources of blood glucose. Food contains glucose, usually ingested in the form of starch or dissaccharides and is converted to glucose by enzymes. The liver can also synthesize glucose from other food nutrients such as simple sugars or amino acids which are derived from protein digestion. Therefore, the blood level of glucose is a summation of the functions of its rate of entry into the blood and its rate of removal. The prior means of control of the blood level is summarized as follows:

| Prior Knowledge Limits in Regulation of Blood Glucose Levels | |
|---|---|
| Factors that Elevate Glucose | Factors that Lower Blood Glucose |
| 1. Ingested Food (i.e., starch, sugar) | 1. Fasting and Exercise |
| 2. Hepatic Glucose Production | 2. Hormone Stimulated Glucose removal from blood. |
| a. Glucose release from glycogen stimulated by glucagon, nor-epinephrine or epinephrine. | a. Insulin stimulates muscle and fat cells to take up glucose. |
| b. Glucose synthesized by glucagon stimulation from protein. | 3. Hormone medicated inhibition of hepatic glucose production. |
| | a. Insulin alone inhibits the glucagon stimulated production of glucose by the liver - both synthesis and release. |

Insulin is a well-known polypeptide hormone that was discovered in 1922. Insulin is released from the beta cells of the pancreas in response to elevated blood glucose. Insulin has the known actions of (1) inhibiting the denovo synthesis and release of glucose from the liver and (2) stimulating the uptake of glucose by muscle and fat tissues. Therefore, insulin has the net effect of lowering blood glucose. This invention has its genesis in the recognition that although it is commonly known that the liver stores ingested glucose as glycogen, the hormonal control mechanism for this glucose storage of glycogen has been unknown.

It has been hypothesized that insulin must stimulate the hepatic deposition of glycogen. However, the addition of insulin alone to liver tissue bathed in glucose solutions does not result in glycogen storage as is seen when insulin is added to muscle tissue bathed in a glucose solution. Prior to the discovery upon which the present invention is based, experts in the actions of insulin, based upon many scientific studies, attribute it to be simply an inhibitor of hepatic glucose production.

SUMMARY OF THE INVENTION

The method of using known serotonin blocking agents to implement the discovery that both insulin and serotonin are required to cause the hepatic uptake of glucose, and that a disease which prevents the normal termination of serotonin production when digestion of food terminates production of glucose, will program the liver for uptake when it should begin glucose supply. This invention, therefore, will terminate the serotonin cofactor in timed relationship with termination of glucose supply to the portal vein of the liver.

This invention and discovery has resulted from observation and in vivo testing, in which it has been discovered that insulin alone is not responsible for liver uptake of glucose, but that a cofactor is essential. That cofactor is serotonin. Therefore, according to this invention and discovery, serotonin should be present when there is no peripheral need for glucose and should be absent when the liver is called upon to supply glucose for the peripheral needs.

The method of this invention, therefore, is to supply serotonin antagonist agent and/or agents to block production of serotonin in timed relationship to food ingestion, as symptoms dictate.

The medication of preference is cyproheptadine.

DETAILED DESCRIPTION

Preferred Embodiment Method

Figure 1:
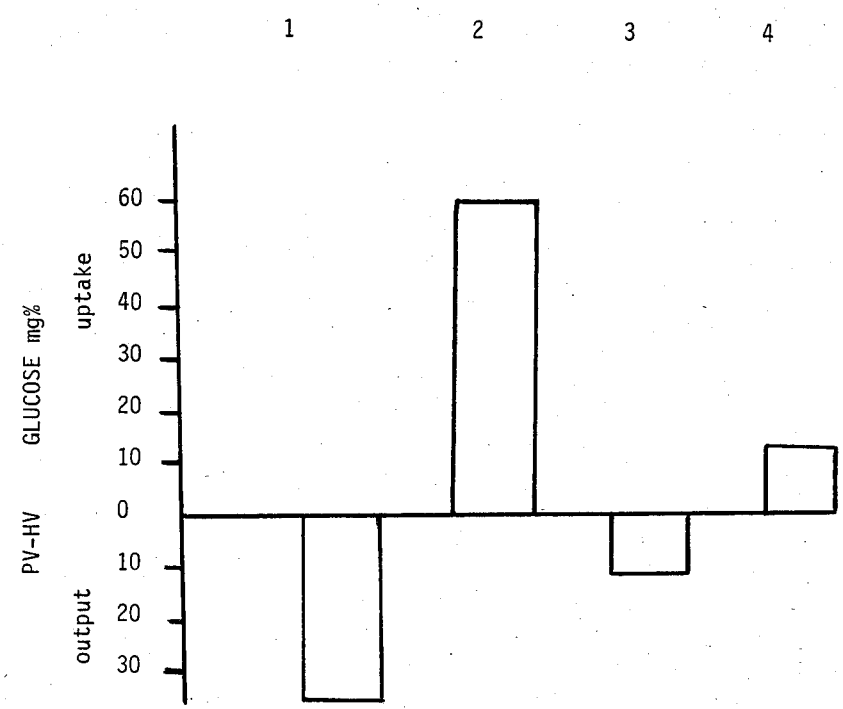
FIG. 1 is a chart which summarizes several clinical tests conducted in this study.

Long and careful study of the liver and its role in disorders and treatments of diseases of glucose metabolism has led to the discovery by this inventor that there is a glucose sensor mechanism in the portal circulatory system that is alerted when the glucose levels of portal blood exceed the glucose values elsewhere in the body.

Portal circulation is that circulatory system in which the portal vein and its branches collect blood from abdominal viscera and convey it to the sinusoids of the liver from which it then passes via the hepatic veins to the inferior vena cava (*Tabor's Cyclopedic Medical Dictionary*, F. A. David Company, 1982).

The discovery further embraces the new and novel concept that insulin alone is not the control that regulates production and storage of glycogen in the liver, and the controlled conversion of glycogen to glucose for release to the blood. Studies have led to the discovery by this inventor that there is a joint factor which cooperates with the insulin; that factor is serotonin (5-hydroxytryptamine or 5HT).

Serotonin is a hormone widely distributed throughout the warm-blooded animal body and is a necessary hormone for a number of bodily functions. For example, serotonin has the normal function of causing small blood vessels to constrict in the area of a hemorrhage. The smooth muscle of the alimentary tract is naturally stimulated by serotonin and thus participates in the normal control of intestinal motility. The heart is stimulated by serotonin to beat both more vigorously and rapidly. These actions of serotonin are well known and have been recently reviewed (Goodman & Gilman's *The Pharmacologic Basis of Therapeutics*, 6th Edition, Macmillan Publishing Co., New York, 1980, pp. 633-639).

According to the research leading to this invention, it has also been hypothesized that serotonin is a circulating hormone that is released into the portal circulation during the absorption of carbohydrate-containing food. The hypothetical relationship of serotonin to sugar intake in the liver has not been appreciated and, hence, medical literature lacks instruction of the etiology of disease such as hypoglycemia in the cooperation of insulin and serotonin in liver and blood sugar functions.

Hence, such research as directed by the hypothesis has led to an understanding of the etiology of hypoglycemia in particular and the serotonin relationship to liver functions in general.

This new hypothesis has led to the discovery that, upon ingesting food, the body senses a greater concentration of glucose in the portal circulation than in other circulatory systems. The only time the portal glucose level is higher than the peripheral level is when food is being absorbed after a meal. As a result, serotonin is produced and carried with the glucose in the portal blood to the liver. According to this invention, the serotonin works in conjunction with insulin to cause the liver to convert the excess glucose absorbed from the meal to liver glycogen for use as glucose by the body during periods of fasting.

It has been established, according to this invention, that in the absence of serotonin, the liver, even though supplied with an adequate amount of insulin, fails to properly convert the ingested glucose in the portal blood to glycogen and store it in the liver. The glucose is passed on from the liver to the rest of the body. The absence of serotonin in this case causes diabetes mellitus.

It has also been established by the discovery of this invention that as long as serotonin is supplied to the liver in the presence of proper insulin levels the conversion of glucose to glycogen will not stop. If this occurs when food is not being absorbed, the liver takes up glucose instead of producing glucose, and the disease hypoglycemia occurs.

If the blood sugar falls to dangerously low levels, the body releases epinephrine and glucagon to counteract the serotonin and insulin effect, but only until the blood glucose is raised to usual fasting levels. At that time the epinephrine and glucagon release is stopped and the serotonin and insulin effect continues and hypoglycemia again occurs. The cycle of sympathetic release then repeats, followed again by the hypoglycemia, etc.

The disease hypoglycemia has been noted in medical literature to be without known cause. Insulin excess can cause hypoglycemia, but this occurs only rarely. According to the discovery of this invention, the common cause of hypoglycemia is the inappropriate release of portal serotonin when intestinal glucose absorption has ceased. Since insulin is nearly always present in the portal blood, its combined effect with the inappropriately released serotonin is to stop hepatic glucose production and start hepatic glucose storage. This situation leads to hypoglycemia since in the fasting state the liver is the body's only source of blood glucose.

The body must avoid hypoglycemia and have adequate sources of glucose for energy. The brain, for example, must have an adequate and constant supply of glucose. A failure to have adequate glucose for the brain is as catastrophic as not having enough oxygen. A deprivation of glucose for only a few minutes can lead to irreversible organic brain damage.

When hypoglycemia occurs the body invokes an emergency hormone system, the adrenergic system, which temporarily stops the hepatic glucose uptake and switches the liver to producing glucose for the rest of the body. The adrenergic hormones that do this also cause the well-known "fight and flight" symptoms of agitation, sweating, and other symptoms that are a common feature of hypoglycemia. In fact, the symptoms of hypoglycemia are not really due to the low levels of blood glucose, per se, but due probably to these adrenergic hormones.

Adrenergic nerve stimulation (epinephrine and norepinephrine) and glucagon can convert the liver from glucose uptake even in the presence of serotonin. However, this adrenergic (sympathetic) nerve response stops after glucose values reach the normal fasting level. If the serotonin release is continuing, then the hepatic glucose uptake returns and another hypoglycemic episode occurs, to be followed by another sympathetic response, etc., not to be broken until food is eaten.

Thus, this invention has established that to control hypoglycemia the production of serotonin must be stopped or means supplied to block the effect of the serotonin after a sufficient amount of conversion and storage of glucose has been accomplished, and before the blood sugar level of the patient has fallen below acceptable levels.

It must be understood that in making this disclosure of the normal physiological control mechanisms of the body there is no clear understanding by the medical profession of all cause and effect leading to the symptoms of the disease known as hypoglycemia. There is certainty, however, of the control by means of this invention.

Reactive or functional hypoglycemia is a disease classification which is an association between the well-known symptoms and an abnormally low blood glucose. This association between symptoms and the biochemical abnormality of low blood glucose is not easily demonstrated. In fact, clinical investigators have had great difficulty in proving beyond all of their doubt that the symptoms are really due to the hypoglycemic state.

The real situation, physiologically, as has been established according to this invention:

1. Hypoglycemia occurs in response to an inappropriate release of portal serotonin.

2. The decrease in glucose level may be enough to trigger the compensatory sympathetic nervous system response, but not low enough to be considered "hypoglycemic" by the usual biochemical values. In other words, any one particular individual's norms may be narrower than the population norms. Biochemically this is a real problem because in a majority of cases there is no way to biochemically diagnose the disease. The fact that biochemically one cannot diagnose the problem of low blood sugar does not prevent the adequate treatment of "hypoglycemic symptoms" according to the teaching of this invention with serotonin antagonists, i.e., cyproheptadine.

Therefore, this invention is successful for both situations: (1) symptoms correlated with low blood glucose values and (2) symptoms without corroborating laboratory data.

According to the hypothesis of this discovery, the symptoms of hypoglycemia should occur after the lowest level of blood glucose and not simultaneously with it since the symptoms are probably due to adrenergic response and not hypoglycemia. This might explain the lack of correlation between symptoms and biochemical low blood glucose that troubles the present medical practitioner.

To prove the roll serotonin plays in improper uptake, it is first necessary to establish the total roll serotonin plays. Hence, the immediately following experiments are to establish that without serotonin, little or no glucose is taken up and stored by the liver.

The necessity for the introduction of serotonin into the portal vein in order to cause the hepatic storage of glucose eaten in a meal has been proven in two different studies in a dog model which mimics the early stage of adult onset diabetes (Type II). In this model, adult onset diabetes, conventionally thought to be caused solely by lack of hepatic insulin, was induced in healthy mongrel dogs by selective denervation of the glands which secrete serotonin into the portal vein blood during a carbohydrate meal. These serotonin glands respond through the nervous system when glucose is being absorbed into the portal blood from the small intestine, and they normally cease producing serotonin when the meal has been absorbed.

In the first study a normal dog was anesthetized and catheters were surgically placed in the portal (the main blood supply to the liver) and hepatic veins (the main blood vessel leaving the liver) for the purpose of simultaneously measuring the glucose levels of the blood entering and exiting the liver. If the glucose level is higher in the portal than the hepatic vein, the liver is taking up and storing glucose. If, on the other hand, the hepatic vein glucose level is higher than the portal vein the liver is producing (releasing) glucose to supply the glucose needs of the rest of the body. The chart of FIG. 1 summarizes the several clinical test conducted in this first study.

This study teaches that the normal delivery of the 5HT in the portal vein to the liver can be surgially terminated. The deficiency of 5HT thus created produces the effect of continuous hepatic glucose output. Then, by direct delivery of 5HT to the liver by intraportal infusion and the resultant hepatic uptake, it is established that serotonin is, in fact, necessary along with insulin to cause hepatic glucose uptake.

Figure 2:
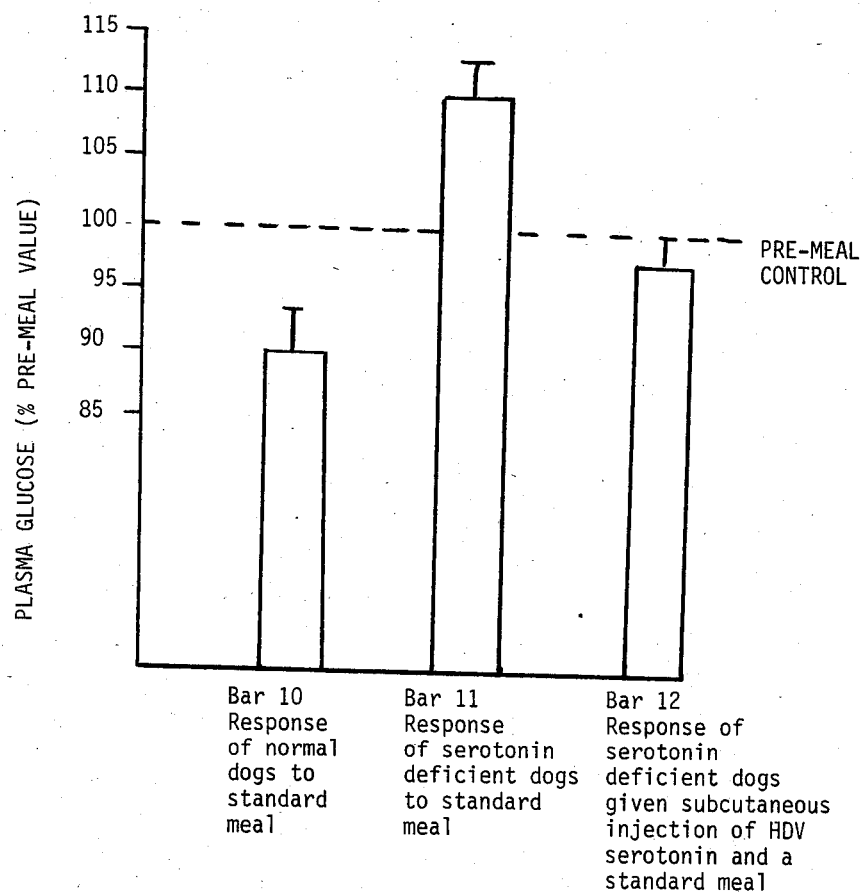
FIG. 2 is a graph of an average obtained from four dogs studied over several weeks using themselves as controls, followed by demonstration and this stabilization of this invention.

A second study used four healthy mongrel dogs to demonstrate this role of serotonin in glucose metabolism. The dogs were studied over several weeks using them as their own controls. The dogs were given a standard meal followed by taking peripheral venous blood samples at hourly intervals for four hours. The data are expressed as an average of the four dogs. This data is depicted in the FIG. 2.

Several days later the dogs were injected subcutaneously with a small dose of serotonin (0.5 microgram serotonin/kg body wt) in the vesicle delivery system of the U.S. application Ser. No. 456,270 filed Jan. 6, 1983. This means of delivery was chosen because free serotonin is so avidly taken up by the peripheral tissues of the body that the free serotonin fails to reach the liver. Immediately following the injection of the HDV-serotonin the dogs were given the standard meal followed by hourly blood samples for glucose. Bar 12 clearly shows that the dogs' responses to the serotonin delivered to the hepatocytes and the meal were more like their normal pre-denervation response (bar 10) and statistically lower than the post denervation (no serotonin) response (bar 11).

The conclusion from these two studies was that serotonin is a hepatic neuromediator required for the normal response of hepatic glucose storage during a carbohydrate meal. The corollary to this conclusion is that serotonin in the portal blood during times of fasting, along with insulin which is nearly always present, would result in an inappropriate hepatic uptake of glucose and, therefore, hypoglycemia, since the blood's (and the body's) glucose comes only from the liver. That is to say that if the liver is storing glucose, it cannot simultaneously be supplying glucose. The tissues of the body are at the same time consuming glucose; therefore, hypoglycemia occurs. If, therefore, serotonin at the liver caused hypoglycemia, a serotonin antagonist at the liver should prevent hypoglycemia. It may be fairly stated that this invention resides as much, or more, in the discovery of the cause and effect of hypoglycemia, as it does in the means to correct the malfunction.

The hypothesis described has been confirmed in vivo in a human patient. At the present stage of the art, hepatocyte directed vesicle treatment as taught by U.S. application Ser. No. 456,270 filed Jan. 6, 1983, is not available for use in a human patient. Dogs have been used to test the invention, and the dogs could be and were controlled with hepatocyte directed vesicles as taught by U.S. application Ser. No. 456,270 with exceptional results.

In the human patient, Cyproheptadine as an oral medication was employed. As set forth below, the tests made on the human patient by oral dosing proved the point of the invention, but the patient was subject to serotonin suppression over the entire body also. This suppression generally is acceptable for limited periods of time but would be less desirable for long-term use.

Cyproheptadine is a derivative of dibenzo (ae) cycloheptatatriene (U.S. Pat. No. 3,014,911; Merck Index, 8th Ed., 1968, p. 316). Prior to this invention, Cyproheptadine has been primarily used as an antiallergic, antipruritic agent. It is a known serotonin and histamine antagonist. It also has use in post-gastroectomy dumping syndrome and intestinal hypermobility, as well as having a mild central depressant property (Goodman and Gilman *Pharmacological Bases of Therapeutics*, 6th Ed.).

It was hypothesized that if the general depression of serotonin would cause the liver to change from glucose output to glucose uptake, then it could be safely concluded that serotonin is in fact a cofactor with insulin in causing the liver to uptake the glucose food supply and in the absence of serotonin, the liver would begin to output into the peripheral system.

In the human test, the patient kept a log of the relationship of ingested food and the onset of hypoglycemic symptoms to establish an average time of symptomatic onset factor. The serotonin blocking agent or antagonist was then taken after eating but prior to the established average onset factor. Patients must be treated individually as body chemistries differ, but in non-treated patients, approximately two to three and one-half hours after eating, hypoglycemic symptoms of acute fatigue, restlessness, malaise, marked irritability and weakness begin to appear. Severe symptomatic cases may be characterized by mental disturbances, delirium, coma and possibly death. Therefore, using the three to three and one-half hour time period a guideline, symptomatic onset can be predicted within thirty to sixty minutes in nearly every case, and the blocking agent is then administered approximately 45 minutes before the expected onset. The actual timetable successfully used by the human patient is set forth hereinafter.

Cyproheptadine, or any other serotonin-blocking or suppressing agent, has not been used prior to this invention to suppress serotonin in timed relationship to food intake for the termination of glycogen storage in the liver.

Thus, an extremely important and novel new use has been discovered for an old and well-known chemical substance which functioned to block serotonin. Cyproheptadine has not heretofore been administered knowingly to patients to control the uptake of glucose by the liver.

Hence, a new treatment for hypoglycemia has been discovered using a serotonin blocking agent, administered in timed relationship to an empiracally determined body function whereby glucose storage is terminated and liver supply is glucose to the body initiated. It has been established that blocking the production, storage, or function of serotonin by any means will produce the desired liver function control, but Cyproheptadine is preferred because of its known low side reaction potential.

Functional hypoglycemia is due to a release of portal serotonin at a time when gastrointestinal absorption has been completed. The insulin which is correctly present in the portal blood at this time to normally inhibit hepatic glucose production, acts in concert with serotonin to stimulate hepatic glucose uptake. Since there is then no source of glucose for the body (food absorption has ceased and the liver is in uptake) the utilization of glucose by the body depletes the available surplus and produces hypoglycemia.

The body reacts to severe hypoglycemia with a large release of adrenergic mediators and glucagon. These agents stop the action of serotonin and convert the liver to producing and releasing glucose to supply the body's needs.

However, this defense system causes the well known fight and flight response. Blood glucose goes up and down cyclically in response to serotonin, then adrenergics, then serotonin, etc. The control is poor and the patient is in obvious distress.

The preferred means of therapy for hypoglycemia of this type is a specific blockage of the serotinergic receptor of the hepatocyte by serotonin antagonists. Two examples of oral ingested blockers are methysergide and cyproheptadine. Of these two examples, methysergide is less preferred because of greater possibility of undesirable side effects. Both agents block serotonin's effects on hepatic glucose uptake. The selected agent is administered thirty to sixty minutes prior to the onset of symptoms (these are readily predicted by the patient). Full relief is thus obtained.

An actual dosing schedule and response obtained from the hypoglycemic patient treated with cyproheptadine:

9:00 a.m.—Eat breakfast
10:30 a.m.—Take Cyproheptadine 4 mg
11:00 a.m.—Usual onset of symptoms-blocked
12:00 p.m.—Lunch
3:30 p.m.—Take Cyproheptadine 4 mg
4:00 p.m.—Usual onset of symptoms-blocked
5:30 p.m.—Dinner
9:00 p.m.—Take Cyproheptadine 4 mg
9:30 p.m.—Usual onset of symptoms-blocked
11:00 p.m.—Snack
3:00 a.m.—Take Cyproheptadine 4 mg
3:30 a.m.—Usual onset of symptoms-blocked The oral dose of cyproheptadine used was 4 mg for the adult patient. The dosage should be adjusted up or down according to the patient's response. Children require a dosage based upon body weight. A starting dose for children should be 0.025 mg/kg body weight, and up to four doses per day are useful. As with the adult, the dosage should be adjusted to meet the needs of the individual patient indicated by the patient's response.

Cyproheptadine is a serotonin antagonist and is the preferred material. Other agents in this class are methysergide (a derivative of lysergic acid); indole compounds such as gramine, hormine and tryptamine; arylguanides and biguanides; histamine $H_1$ blockers of the ethylene diamine type; phenothiazines such as phenoxybenzamines.

Less preferred but workable means to treat hypoglycemia include drugs which generally lower body levels of serotonin. These include the following:
1. Drugs which inhibit serotonin synthesis:
   a. para chlorophenylalanine
   b. para chloroamphetamine
   c. amino acid derivatives of 6-fluorotryptophan
2. Drugs which inhibit serotonin membrane uptake:
   a. tertiary amines such as chloroimipramine, imipramine and amitriptyline
   b. fluoxetine
3. Drugs which inhibit serotonin storage:
   a. reserpine
   b. tetrabenazine c. fenfluramine While serotonin antagonists such as cyproheptadine are the preferred class for treating and preventing hypoglycemia, it must be recognized that they block all serotonin actions all over the body and thus may induce many side effects such as sedation, sleepiness, dizziness, disturbed coordination, confusion, restlessness, rashes, blurred vision, hypotension, anemias, anorexia, to name a few. These nonspecific effects of this class of materials can be overcome by utilizing a bipolar lipid membrane delivery system specific for the hepatocytes to deliver these materials only to the serotonin receptors responsible for the glucose effects in the liver. Thus, all other serotonin mechanisms in the body remain unaffected. This hepatocyte delivery of serotonin antagonists is the ultimate form of treatment for hypoglycemia. The hepatocyte delivery vesicle is taught in U.S. patent application Ser. No. 456,270 filed Jan. 6, 1983.

What is claimed is:

1. The method of treating a warm-blooded animal having an abnormal liver uptake of glucose resulting in low levels of glucose in the peripheral system with symptoms of hypoglycemia, which comprises administering to said warm blooded animal having abnormal liver uptake of glucose, a therapeutic dose of cyproheptadine.

2. A method of treating hypoglycemia in a warm-blooded animal caused by excess serotonin being present in the portal venous blood after the level of glucose present in the portal venous blood has dropped due to the substantial completion of absorption of carbohydrate-containing food from the gastrointestinal tract, by administering to said warm blooded animal having hypoglycemia caused by excess serotonin, a serotonin inhibiting amount of cyproheptadine, thereby inhibiting glucose uptake by the liver and providing glucose for the peripheral blood supply.

3. The method of claim 2 wherein the serotonin antagonist cyproheptadine is administered to the host within 2 to 4 hours after ingestion of food.

* * * * *